United States Patent [19]

Wadsworth

[11] Patent Number: 4,691,704

[45] Date of Patent: Sep. 8, 1987

[54] LIGATURE TOOL AND PROCESS FOR CASTRATING LARGE ANIMALS

[76] Inventor: Le Grand D. Wadsworth, Rte. 1, Box 168, St. Ignatius, Mont. 59865

[21] Appl. No.: 914,740

[22] Filed: Oct. 3, 1986

[51] Int. Cl.[4] .............................................. A61B 1/06
[52] U.S. Cl. ..................................... 128/306; 128/326
[58] Field of Search .................. 128/306, 303 A, 326, 128/320, 346, 307, 311; 383/42, 59, 60

[56] References Cited

U.S. PATENT DOCUMENTS

| | | |
|---|---|---|
| 733,331 | 5/1903 | Hustin . |
| 1,850,906 | 3/1932 | Zins . |
| 1,940,351 | 12/1933 | Howard . |
| 2,125,404 | 8/1938 | Snyder . |
| 2,433,956 | 1/1948 | Miller . |
| 2,610,631 | 9/1952 | Calicchio . |
| 3,547,124 | 12/1970 | Fergusson . |
| 3,687,138 | 8/1972 | Jarvik . |
| 3,726,278 | 4/1973 | Scott . |
| 4,220,155 | 9/1980 | Kimberling et al. . |
| 4,572,179 | 2/1986 | Teitelbaum et al. . |

Primary Examiner—C. Fred Rosenbaum
Assistant Examiner—Gene B. Kartchner
Attorney, Agent, or Firm—Keith S. Bergman

[57] ABSTRACT

A process is disclosed to castrate large mature animals by ligation. A tool for accomplishing the process provides a handle with an elongate body supportin a tightening rod that is moved along the body. The forward body portion defines an orifice that supports a grommet through which elastomeric surgical tubing is inserted with a forwardly extending loop. The rearward portions of the tubing are releasably engaged in the tightening structure which is moved to create tension upon the looped portion and any animal body part carried within that loop. The tool body provides crimping structure that crimps a grommet about the ends of the tensioned surgical tube to fasten it when properly positioned.

6 Claims, 5 Drawing Figures

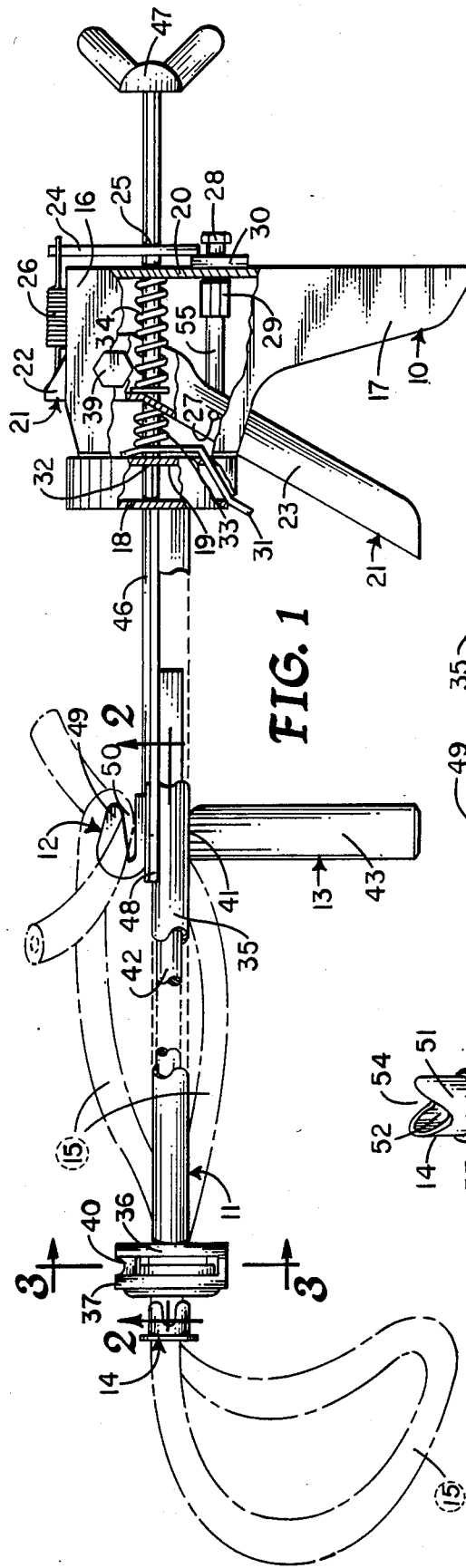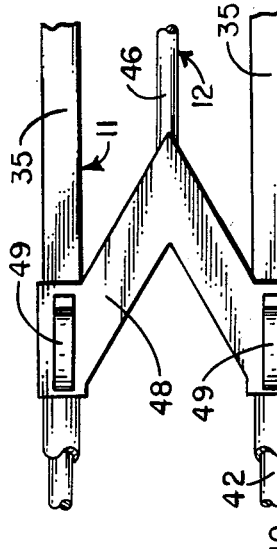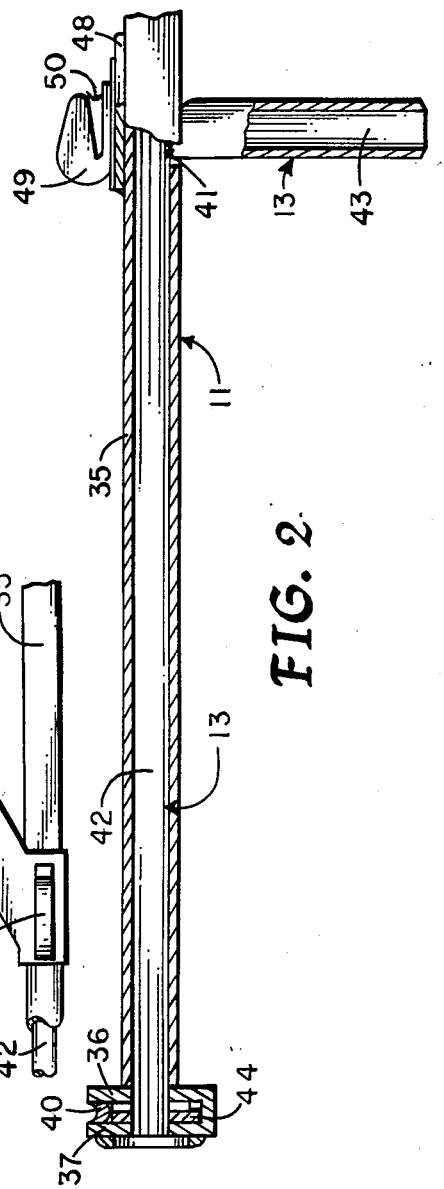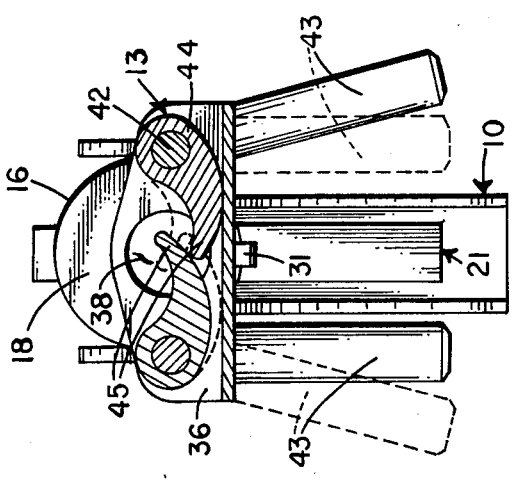
FIG. 1
FIG. 2
FIG. 3
FIG. 4
FIG. 5

LIGATURE TOOL AND PROCESS FOR CASTRATING LARGE ANIMALS

BACKGROUND OF INVENTION

RELATED APPLICATIONS

There are no applications related hereto now filed in this or any foreign country.

FIELD OF INVENTION

My invention relates generally to a ligature tool and process for castrating large animals by use of elastomeric surgical tube as a ligature.

BACKGROUND AND DESCRIPTION OF PRIOR ART

Ligation has long been used in animal husbandry and surgery to cause the atrophy of a body part exterior of the ligation site. Generally such areas, at least in the higher animals, when cut off from systemic control and supply, atrophy quite readily, usually within a couple of weeks, and the ligation site substantially heals quite effectively by the time of atrophy. This procedure has heretofore been known and used in higher animals, including man, for various purposes.

The procedure is admirably suited to the castration of animals having external testicles carried in a scrotal pouch, such as bovines, horses, goats and sheep, and has been used for such purposes. The process is relatively safe as it does not require any surgical invasion of the animal's body and it is relatively simple so that it can be performed by nonexpert and relatively untrained personnel. Normally by the time atrophy of the scrotal pouch and its contents occurs, the ligation site will be substantially healed and will not be particularly subject to microbal invasion nor will it be an attractant to various insects and vermine that might harm an animal.

The process, as heretofore known in the animal husbandry arts, has generally been confined to smaller, younger animals. The ligature applied in such cases has most commonly been an endless, elastic band which by reason of its nature has tended to limit the process to smaller animals. Various tools have heretofore become known to apply such endless bands to an animal, but by reason of the anatomy of the animal and the nature of the ligature, the scrotal sac containing testicles must be passed through the band. Since all elastic materials have limits of elasticity, theses limits have essentially determined the size of scrotal pouches and testicles upon which endless elastic bands may be used. This inherent limitation has restricted use of this castration process to smaller and generally younger animals.

Ligation other then by endless elastic bands has been known in surgery, but the process has not generally been used upon larger body parts for various reasons, and similarly it has not generally been used in the animal husbandry arts for castration. Such castrating tools and processes that have not used an endless elastic band have generally used an elongate non-elastic element of one sort or another and those few that have used an elastic ligature have required the use of some relatively, large, clumsy apparatus that must be carried by an animal during the period of ligature use. In animal husbandry generally such devices are not effective or efficient, if in fact useful, as an animal may disengage them or tear the parts involved, and an animal's contact with external objects, either deliberate or accidental, may have the same results. If a ligature or its associated apparatus tends to tear any of the body parts involved during the ligation process, it ceases to have utility and, in fact, becomes a detriment such as might cause harm or even death to the animal involved.

With this background in mind, the instant invention was conceived to provide both a process and tool for the castration of large, mature animals having scrotal pouches of substantial size, especially bulls and stallions or larger rams or billies.

My process generally provides a ligation band of elongate, endless elastic material that is established about the interconnecting area of a scrotal pouch with the body of an animal. The elastomeric material forms a loop through an annular grommet that is fastenable thereabout by crimping to permanently establish the elastomeric loop in place, once properly positioned with appropriate tension. The crimped fastening grommet is small and both it and the ligation loop are semipermanently established so that they generally may not be removed generally by an animal or its activities, at least to any greater extent then an endless elastic band. The elastomeric loop, however, may be initially established at any size desired for positioning and may be thereafter moved by my apparatus to form a relatively small stressed loop of appropriate size and tension to accomplish its purpose. The prior art has not generally provided a process wherein an elongate elastomeric member is formed into a ligation element during the process of placement or such an element that does not have larger associated structures which may be removed by or harm an animal being operated upon.

My apparatus is distinguished from the prior art in that it provides a handle and trigger structure with an elongate body extending forwardly therefrom to define a forepart with an orifice to carry a crimpable annulus through which a loop of elastomeric ligation tubing is formed. The structure further provides a tightening rod movable along the body rearwardly of the crimping grommet to tighten the loop of ligation tubing forwardly thereof and a crimping structure associated with the body to crimp the grommet in permanent position on the elastomeric ligation tubing when properly positioned. The prior art in contra-distinction has generally provided an endless elastomeric band with an associated tool having structure necessarily limited to the stretching of that band to allow its placement over the scrotal pouch and testicles of an animal by moving the band thereover to a position at the intersection of the scrotal pouch with the animal body. Such structure by its essence must expand a pre-formed endless elastomeric band and is therefore essentially distinguishable from my structure which forms a loop from endless material in much larger then final form and then moves the loop material to make the loop smaller and to create tensive forces therein with subsequent mechanical fastening of its ends.

My tool is relatively small and of an elongate nature to allow it to be readily operable at a spaced distance from the animal area being operated upon so that the tool may be easily used upon an animal without interference from various parts of the animal, in contra-distinction from the use of the known endless band applicators. The initial loop established with my apparatus before application to an animal may be of any desired size and particularly may be sufficiently large to allow application to the scrotal pouch of any animal, be it many inches in diameter as in the case of a large, mature bull or stallion. The tool may quite as readily, however, be applied to a scrotal pouch of smaller size without any particular limit.

My tool uses ordinary elastic surgical tubing for its ligation element so as to make this element readily available and of relatively low cost and substantial strength and durability. The crimpable grommet that fastens the ends of my ligation loop together provides a relatively permanent fastening that generally cannot be disrupted by an animal or its activities, is relatively small so as to be of insignificant effect upon an animals activities, and is relatively inexpensive. My tool provides a trigger operation which allows the generation of substantial tensioning forces with a minimum of operator effort.

All of these features distinguish my invention both structurally and functionally from the prior art, but this distinction resides not in any single element per se, but rather in all elements synergistically combinated to provide the functions specified.

SUMMARY OF INVENTION

My process generally provides for the ligation of an external scrotal pouch of an animal by means of an elastic element and my tool provides means for creating such a ligature in place from endless material. The process is adapted for use on larger animals by providing an elongate, elastic ligature element which may be initially formed with a loop of any size and thereafter tightened to create necessary size and tension to accomplish its purpose, so that it may service mature animals of any size, as well as smaller animals.

My apparatus provides a trigger-type handle having an elongate body extending forwardly thereof with a forwardmost plate defining a medial orifice to carry a crimpable annulur grommet. The tool body provides mechanism for crimping a grommet. A tightening structure moves along the body responsively to handle trigger motion and has means of releasably fastening the ends of an elastomeric ligation element thereto.

To use the tool, a crimpable grommet is established in the forward body plate and an elastomeric ligature element is formed into a loop with both ends passing rearwardly through the crimpable grommet and releasably fastened to the tightening structure. The tool is then established with the ligature loop about the juncture of the scrotal pouch of an animal with its body by passing the scrotal pouch and its contents through the ligature loop. The trigger mechanism is then operated to tighten the ligature element until sufficient tension has been created to allow the ligature to accomplish its purpose. The crimpable grommet is then crimped, the ends of the ligature element are released and the tool removed. The ends of the ligature are trimmed at the grommet and the operation is completed.

In creating such a process and apparatus, it is:

A principal object of my invention to provide a process for castrating large animals by ligation of the scrotal pouch and contents by providing an elongate elastic ligature element that may be formed into an initial loop of any desired size and thereafter tightened to serve its purpose.

A further object of my invention to provide such a process that creates a ligature at the juncture of the scrotal pouch of an animal with its body that is small, neat and substantially non-removable so that it may not be removed by the animal or by the animal's activities relative to objects it may contact.

A further object of my invention to provide a tool for such process that is of an elongate nature with its operating elements at a spaced distance from the area being operated upon so that they are conveniently accessible by an operator during operation.

A further object of my invention to provide such a tool that forms a tensed, elastic loop at the site of ligature from ordinary surgical tubing and a particular crimpable grommet that is not substantially more bulky then an oridinary endless elastomeric band.

A still further object of my invention to provide a particular crimpable type annular grommet to permanently fasten the ends of tubing type ligature material together to allow its use for the purposes of my invention.

A still further object of my invention to provide such a tool that is operated by a handle and trigger mechanism that creates substantial tensioning forces necessary in an elastic ligature element with ease and no substantial exertion by an operator.

A still further object of my invention to provide such a device and process that are of new and novel design, of rugged and durable nature, of simple and economic manufacture and operation, and otherwise well suited to the uses and purposes for which they are intended.

Other and further objects of my invention will appear from the following specification and accompanying drawings which form a part hereof. In carrying out the objects of my invention, however, it is to be understood that its essential features are susceptible of change in design and structural arrangement with only one preferred and practicle embodiment being illustrated in the accompanying drawings as is required.

BRIEF DESCRIPTION OF DRAWINGS

In the accompanying drawings which form a part hereof and wherein like numbers of reference refer to similar parts throughout:

FIG. 1 is a partially cutaway orthographic side view of my tool showing various parts, their configuration and relationship from this aspect.

FIG. 2 is an elongate vertical cross-sectional view through the forward body portion of my tool, taken on the line 2—2 of FIG. 1 in the direction indicated by the arrows thereon.

FIG. 3 is a vertical cross-sectional view taken through the forward body structure of the invention of FIG. 1, on the line 3—3 in the direction indicated by the arrows thereon.

FIG. 4 is a partial top view of the medial portion of the body and tightening structure of the tool of FIG. 1 showing details and relationships of these structures.

FIG. 5 is an isometric view of an annular crimping grommet of my invention.

DESCRIPTION OF THE PREFERRED EMBODIMENT

My invention generally provides handle 10 carrying trigger mechanism and structurally communicating with peripherally defined elongate body 11 extending forwardly thereof. The forward portion of the body carries grommet 14 through which ligation material 15 is looped forwardly so that its rearward ends, carried by tightening structure 12, may be moved by the handle trigger mechanism to create tension therein. The grommet is fastened by crimping structure 13 to form a stressed ligation loop.

Handle structure 10 provides horizontal handle body 16 structurally communicating with perpendicularly depending handle element 17, both peripherally formed to define internal chambers to carry the various operative mechanism associated therewith. The handle body provides forward wall 18 and medial wall 19 at a spaced distance rearwardly thereof. Handle back 20 communicates between the handle body and handle element to form the rearward portion of those structures. The handle element in its forward portion defines a chamber for entry of trigger 21 in the rearward course of pivotal motion of that trigger.

The trigger mechanism associated with the handle structure provides means of moving tightening rod 46 of the tightening structure and is of a type heretofore known, especially as for use in caulking guns and like structures. It provides elongate bell-crank like trigger 21 having its upper portion 22 extending through an appropriate orifice above the top portion of handle body 16 and its lower portion 23 extending through an appropriate orifice in the lower part of the handle body. The trigger is pivotally mounted within the medial chamber of the handle body by bolt 39 extending therebetween. Tightening rod 46 extends through orifices defined in the forward and medial handle body walls, through an orifice defined in the forward portion of trigger structure 21, through an orifice in rearward wall 20 of the handle structure, and some distance rearwardly thereof.

Vertically oriented toggle plate 24 defines orifice 25 so that it may fit over tightening rod 46 at a spaced distance rearwardly of, and substantially parallel to, rearward handle wall 20. The upper portion of toggle plate 24 structurally joins extension spring 26, which extends between that plate and upper portion 22 of trigger structure 21, to bias the upper portion of the toggle plate forwardly as the lower portion of the trigger moves rearwardly. The medial portion of trigger structure 21 pivotally supports toggle pin 55 by means of fastening pin 27 extending therebetween. The toggle pin 55 extends rearwardly through an orifice in rearward handle wall 20 and some distance therebeyond so that its end is rearwardly of the toggle plate. Toggle pin 26 carries head 28 at its rearward end and motion limiting sleeve 29 at a spaced distance forwardly of rearward handle wall 20. Spacing washer 30, carried about the toggle bolt on the rearward surface of rearward handle wall 20, limits the forward motion of toggle plate 24 which extends downwardly a distance sufficient to contact the washer 30 but not sufficiently to contact diametrically smaller toggle pin head 28.

Bell-crank like release arm 31 is supported about tightening rod 46 through an appropriate orifice in the handle body. This release lever is of the complex, somewhat "L" shape illustrated, so that its body portion is at a spaced distance rearwardly of medial body wall 19. Its lower portion extends through appropriate slots defined in the forward and medial body walls, so that lower portion projects forwardly and downwardly through the forward body wall. The orifice 32 defined in this release arm for the medial tightening rod 46 is so defined that when in its normal biased position, the release arm will allow the tightening rod to move rearwardly but will not allow it to move forwardly, but when the lower portion of the release arm is moved forwardly, it will allow the tightening rod to move forwardly relative to the handle structure, all as known in the prior art.

Compression spring 33 is carried about tightening rod 46 between release arm 31 and forward portion of trigger mechanism 21 to bias the release arm to its position allowing the tightening rod to move only rearwardly. Compression spring 34 is carried about the tightening rod, rearwardly of washer 34 which is immediately rearwardly of the forward wall trigger structure 21 and the rearward handle wall 20, to bias trigger structure 21 to a forward position but allow its limited rearward motion. This structure as heretofore known, upon operation of trigger 21 will cause the tightening rod to move rearwardly but will not allow it to move forwardly unless and until released by motion of release arm 31.

Elongate body structure 11 provides hollow side tubes 35 structurally communicating with forward body wall 18 of the handle structure and extending forwardly therefrom. The forward portions of the side tubes are structurally joined by inner forward plate 36 extending therebetween. Forward plate 37, positioned parallel to and at a spaced distance forwardly of the inner plate, is structurally joined and maintained in spaced relationship with the inner plate by spacing elements 40 extending therebetween. Both forward plates 36, 37 define axially aligned, medially positioned grommet holes 38 to receive grommet 14 in a nice fit therein. Each tube defines a handle orifice 41 in its lower medial portion, to allow passage and appropriate motion of crimping rod handles 43.

Crimping structure 13 provides elongate crimping rods 42 of a diameter appropriate to pivotally fit within the medial channel defined by side tubes 35. These crimping rods normally extend substantially throughout the length of the side tube carrying it, but at least from outer forward plate 37 rearwardly of handle orifice 41 defined therein. Crimping rods 42 carry depending elongate handles 43 positioned to communicate through handle orifice 41 in side rods 35. These handles are structurally joined in irrotatable fashion to the crimping rod, as illustrated in FIG. 2. The forward portion of the crimping rod, in a position between inner and outer forward plates 36, 37, irrotatably carry crimping dogs 44 sized and configured as illustrated in the cross-sectional view of FIG. 3. The forwardmost portion of the crimping rods bear in outer forward plate 37 for pivotal motion and are carried in appropriate orifices in inner forward plate 36. Normally side tubes 35 do not extend forwardly of inner forward plate 36, but if they should, appropriate orifices (not shown) would have to be created in those tubes to allow passage and motion of crimping dog 44. The crimping dogs are sized and configured substantially as illustrated with tip portions 45 extendible inwardly to about the axis extending between grommet holes 38 in the forward plates, and they are journaled to allow pivotal motion to the position of the axis extending through those grommet holes, as shown in dotted outline in FIG. 3, to allow the dogs to properly crimp grommet 14 about a tensed ligature therein. A single crimping dog may serve the purposes of my invention, but two dogs co-react more efficiently to provide a better crimped grommet with less operator effort.

Tightening structure 12 provides elongate tightening rod 46 of a length sufficient to communicate from a spaced distance rearwardly of rearward handle wall 20 approximately to inner forward plate 36, as illustrated particularly in FIG. 1. This rod at its rearward end structurally carries tightening rod knob 47 to aid in its manual manipulation when required. The forward portion of the tightening rod structurally communicates with ligature fastening structure providing horizontal, laterally extending fastening plate 48 of width sufficient to extend between and over the upper portions of spaced side tubes 35. This fastening plate at each of its lateral sides carries upwardly projecting fastening hooks 49 defining wedge shaped channels 50 to releasably receive and attach flexible ligature tubing therein. Preferably these slots are wedge shaped and forwardly tapering, with their smallest width something less than half of the diameter of ligature tubing to be used with the particular device. This fastening structure may move forward and rearwardly relative to the body tubes but yet remain slideably supported against gravity displacement by those tubes.

All of the structures of my tool hereinbefore described are formed of some rigid, durable material, preferably a metal such as stainless steel, though undoubtedly they may be formed from other materials having appropriate physical characteristics. If formed from metal, the various elements are structurally joined, as indicated, by welding where appropriate.

Grommet 14 is an annular cylindrical structure, as illustrated particularly in FIG. 5. It provides cylindrical body 51 of an external diameter appropriate to slideably fit within grommet holes 38 defined in the forward plates 36, 37 and defines internal channel 54 of appropriate size to receive two portions of ligature tube therethrough with some deformation but without any substantial constraint. Cap boss 53, diametrically larger than the body, is an annular structure structurally communicating about one end of the grommet to limit the extent of insertion of body 5 in hole 38. The cylindrical body defines opposed, somewhat "U" shaped, diametrically opposed notches 54 in the end opposite cap annulus 53 to aid in crimping of the device about ligature material and make that crimping more effective then it would be without the structure. Normally these grommets are formed of some fairly easily deformable material that retains its shape against some force after deformation. I prefer to form these grommets of copper of a body thickness of about 16 gauge, but undoubtedly other materials, and especially metals having similar characteristics, could be used for the grommet structures, if not so effectively.

Ligation material 15 is an elongate element of substantial strength and elastic deformability, preferably of an annular cross-sectional shape defining a medial channel. The material I found ideally suited for this purpose is ordinary, heavy walled, rubber surgical tubing of approximately ⅜ inch external diameter. This material has admirable physical properties for use with my invention, though undoubtedly other materials of a similar nature may also be usable with it, if not so effectively. The ligation material must not only have appropriate elasticity but must be retentively deformable to allow releasable fastening of my tightening structure. It must also have appropriate surface friction to allow holding in the tightening structure and semi-permanent fastening by the grommet structure.

Having thusly described the structure of my invention, its use may be understood.

Firstly a tool is constructed as specified. The tool for normal purposes is configured and sized substantially in proportion to the illustrations and with an overall length of some 12 inches or thereabout.

To use the tool, tightening structure 12 is released by operation of release arm 31 and moved to a forward position with fastening plate 48 in a forward position immediately rearwardly of inner forward plate 36 of the body structure. A grommet 14 is positioned in grommet holes 38 defined in inner and outer forward plates 36, 37, with its cap annulus 53 forwardmost and its cylindrical body 51 extending rearwardly through the grommet holes. An appropriate length of ligature material is selected and its two ends are passed, from a forward position, rearwardly through the grommet to extend some distance rearwardly of forward plates 36, 37. Each end of the ligature material is then fastened in one of the fastening ears 49 of tightening structure 12 by engaging the material with some deformation within the fastening channels defined therein. A loop of appropriate size to allow passage of the scrotal pouch and contents of an animal to be castrated is left in the ligature material forwardly of the grommet.

With the tool loaded in this condition, manual manipulation is accomplished to pass the scrotal pouch of the animal to be castrated through the loop in the ligature material. If necessary to accomplish this purpose, the ligature material may be manually adjusted by releasing its ends and making the loop larger by pulling the material forwardly through the grommet structure or it may be made smaller by releasing at least one end and pulling the material rearwardly and refastening it in the fastening structure.

Once positioned with the ligature loop about the scrotal pouch of an animal and in a postion approximately at the junction of that pouch with the body structure, trigger 21 is successively operated by pulling the trigger toward the associated handle. As this occurs, tightening rod 46 will be moved rearwardly with each stroke of the trigger, but will retain its position as the trigger moves forwardly for another stroke. The process is continued until the loop in the ligature material forwardly of the forward plate of the body structure is small enough and appropriately tensioned to serve its purpose. At this point, since the loop may not release, the position will be maintained for future operation.

With my tool so positioned and in such condition crimping rod handles 43 are grasped by the operator. The crimping rod handles are pivotally moved toward each other to cause crimping dogs 44 to move inwardly toward the medial portion of the grommet carried in the grommet holes my tool. This causes one of the fastening ears of the grommet to move inwardly, somewhat between the two portions of ligature material extending therethrough, to fasten that material with some pressure against the opposite side of the grommet to cause a permanent fastening of the ends of the ligature material together in the grommet structure. Preferrably to best accomplish this purpose, one of the fastening ears of the grommet is positioned in a vertical position so that it is contacted by and moved inwardly toward the other fastening ear, as this tends to cause a better and more permanent fastening then if some other portion of the grommet structure be moved inwardly and crimped. It should be noted, however, that the sizes and configurations of the grommet and crimping dog are such that crimping may be had with any orientation of the grommet.

Once the ligature material is permanently fastened, release arm 31 of the handle structure is operated to release the tightening rod and that rod is then manually moved forwardly by the operator to release tension in the ligature material rearwardly of the forward plate structure 36, 37. Once the tension in the end portions of the ligature material is released, those ends may be manually manipulated to released them from channels 50 of fastening ears 49, and the tool removed from the ligature material by manually moving it rearwardly away from the ends of that material. Once the tool is removed, the ends of the ligature material may be trimmed immediately adjacent the grommet fastening structure or, if desired, those ends may be cut immediately rearwardly of inner forward plate 37 before removing the tool to make the removal process simpler.

Since in the use of our invention it is necessary to move the ligature material relative to other ligature material and other structures with which it may have surface contact, particularly the grommet, it is oftentimes desirable to apply talcum powder or similar material, as well known in the surgical arts, to reduce some friction. If this not be done, since the rubber tubing has substantial surface friction, its motion may be rather difficult.

Once established as described, the ligature will generally cause atrophy of the scrotal structure and its contents within approximately two weeks and at that time, the scrotal pouch and ligation material will drop off to leave a clean juncture which will be relatively healed at that time. The castration process will be thusly completed.

In using my tool it is to be noted that the expendable materials are relatively inexpensive and the ligation material particularly is readily available in the present day marketplace.

It is further to be noted that the entire ligation structure, once placed, is relatively small and without any protruding portions elements that might catch on external objects or aid an animal in attempting to remove or otherwise affect the structure.

It should further be noted that the ligation loop forwardly of a grommet positioned in the forward body plate structure might be of any particular desired size. It may be made quite large enough to operate upon animals of any size, no matter what the extent of their scrotal pouches or testicles might be, and at the same time it may be made as small as desired to be effectively function upon the smallest of animals. It should be noted that, if the size of the ligation loop need be changed substantially from an initial position, allowing placement over the scrotal pouch of an animal, to a later tensed position, this may be readily accomplished by manipulation of the ligation tubing by manually pulling it rearwardly through the grommet after placement. The same results might be accomplished by pulling it rearwardly by means of the tightening structure and then, if there be not sufficient motion in that structure, by releasing the ligation tubing, moving the tightening structure forwardly and refastening the ligation tubing closer to the grommet to allow a second tightening operation.

It is further to be noted that the ligation material may be tightened quite as much as desired with the only limitation being the elasticity and tensional strength of the material involved, both of which characteristics are quite adequate to fulfill their purposes in thick walled rubber surgical tubing.

It should also be noted that an automatic cutting device for the ligation tubing might be associated with my tool as heretofore known in prior art.

The foregoing description of my invention is necessarily of a detailed nature so that specific embodiments of it might be set forth as required, but it is to be understood that various modifications of detail, rearrangement and multiplication of parts and steps might be resorted to without departing from its spirit, essence or scope.

Having thusly described my invention, what I desire to protect by Letters Patent, and

What I claim is:

1. A tool for castrating animals having an external scrotal pouch by ligation, comprising, in combination:
   a handle structure having an upper handle body with a perpendicularly depending handle element and associated trigger mechanism to move a tightening rod relative thereto;
   an elongate body structure carried by a forward portion of the handle body and extending forwardly thereof with a forward plate structure in the forewardmost part of the body, said foreward plate structure defining a medial axially aligned grommet hole therein;
   tightening structure including an elongate tightening rod with a forward portion having means of releasably fastening ligation material thereto, said tightening structure having a tightening rod communicating through the handle structure and rearwardly thereof;
   means associated with the handle structure to move the tightening rod rearwardly upon operation of the handle trigger mechanism and of restraining forward motion except upon operation of a release arm; and
   means carried by the body structure for crimping a grommet carried in the grommet hole defined in the forward plate structure.

2. The invention of claim 1 further characterized by:
   an elongate ligature forming a loop forwardly of the grommet and having both ends extending through the grommet and rearwardly thereof to be releasably interconnected with the tightening structure so as to allow the loop forwardly of the grommet to be tightened thereby.

3. The invention of claim 1 further characterized by:
   the elongate body being formed by spaced parallel rods defining elongate circularly cylindrical channels therethrough,
   each body rod pivotally carrying a crimping rod and defining an orifice through which a crimping handle structurally communicating with the crimping rod depends, said crimping rods each irrotatably carrying crimping dogs extending inwardly therefrom at a position to contact and crimp a grommet carried in the grommet hole defined in the forward plate.

4. A tool for castrating animals by ligation comprising, in combination:
   a handle structure having an upper handle body with a structurally communicating depending handle element, said handle structure having a trigger mechanism to move an elongate tightening rod extending longitudinally therethrough relative thereto;
   a body structure, including two elongate side rods defining circular cylindrical channels therein, extending forwardly from the handle body to a forward plate structure interconnecting the side rods in their forewardmost parts, said foreward plate structure having spaced parallel inner and outer plates, each of said forward plates defining medial axially aligned grommet holes to receive a crimpable grommet therein;

crimping means including crimping rods pivotally carried in the side rods, said crimping rods structurally carrying crimping dog extending inwardly therefrom between the inner and outer foreward body plates to contract and crimp a grommet carried in the grommet holes defined in those plates and depending irrotatably mounted handles communicating through and externally of the side elements to cause pivotal motion of the crimping rod upon manual manipulation; and tightening structure including an elongate tightening rod having a forward fastening structure, slidably supported on the body side rods, with two ears to releasably fasten the ends of ligature material, said tightening rod extending rearwardly from a spaced distance rearwardly of the outer forward plate through the handle structure and rearwardly therebeyond, and being interconnected with the trigger mechanism to move the tightening rod rearwardly upon operation of the trigger mechanism and not move it forwardly except upon operation of a release arm associated with the trigger mechanism.

5. The invention of claim 4 further characterized by:

a cylindrical deformable grommet, defining fastening ears in one end part and an annular cap boss in the second end part, carried in the grommet holes defined in the inner and outer forward plates and elongate elastically deformable ligation material positioned in a loop extending forwardly of the grommet with each end of said material extending through the grommet and a spaced distance rearwardly thereof, said ligation material ends being releasably interconnected to the fastening structure of the tightening mechanism, so that upon operation of the handle trigger the ligation material is moved rearwardly and the loop forwardly of the grommet made smaller and tensioned.

6. A process for the castration of larger animals by means of endless elastic ligation material, comprising, in combination:

the formation of ligation material in a loop forewardly of a crimpable grommet adapted to fasten the ends of the ligation material together upon crimping, said grommet being carried in a tool having means of moving at least one end of the ligation material rearwardly through the grommet on the side opposite the loop and having second means of crimping the grommet when in fastening position;

manually passing the ligation material over the scrotal pouch and contents of an animal to be castrated;

tightening the ligation material about the scrotal pouch of said animal at a position approximately at the point of contact of the scrotal pouch with the body structure;

crimping the grommet upon the ligation material to fasten the ends thereof together;

removing the tool from the fastened ligation material and trimming the ends thereof adjacent the grommet.

* * * * *